(12) United States Patent
Tixier et al.

(10) Patent No.: US 7,382,456 B2
(45) Date of Patent: Jun. 3, 2008

(54) SPECTROSCOPIC SENSOR FOR MEASURING SHEET PROPERTIES

(75) Inventors: Sebastien Tixier, North Vancouver (CA); Daniel A. Gordon, West Vancouver (CA); Frank M. Haran, North Vancouver (CA)

(73) Assignee: Honeywell ASCA, Inc., Ontario (CA)

( * ) Notice: Subject to any disclaimer, the term of this patent is extended or adjusted under 35 U.S.C. 154(b) by 0 days.

(21) Appl. No.: 11/636,810

(22) Filed: Dec. 11, 2006

(65) Prior Publication Data

US 2007/0153281 A1 Jul. 5, 2007

Related U.S. Application Data

(60) Provisional application No. 60/754,767, filed on Dec. 29, 2005.

(51) Int. Cl.
  *G01J 3/51* (2006.01)
  *G01B 11/06* (2006.01)
(52) U.S. Cl. ............... 356/419; 356/326; 356/429; 356/630; 356/632
(58) Field of Classification Search ............... 356/73, 356/326, 328, 419
See application file for complete search history.

(56) References Cited

U.S. PATENT DOCUMENTS

| | | | |
|---|---|---|---|
| 4,632,553 A * | 12/1986 | Vidrine et al. ............. | 356/451 |
| 4,957,770 A | 9/1990 | Howarth | |
| 5,166,813 A * | 11/1992 | Metz .................... | 359/15 |
| 5,338,361 A | 8/1994 | Anderson et al. | |
| 5,995,235 A | 11/1999 | Sui et al. | |
| 6,281,678 B1 | 8/2001 | Auville | |
| 6,459,488 B1 | 10/2002 | Heffner | |
| 6,515,746 B2 | 2/2003 | Opsal et al. | |
| 6,556,306 B2 | 4/2003 | Jiang et al. | |
| 6,573,999 B1 | 6/2003 | Yang | |
| 6,646,752 B2 | 11/2003 | Chen et al. | |
| 6,961,126 B2 | 11/2005 | Belotserkovsky et al. | |
| 7,088,456 B2 | 8/2006 | Germanenko et al. | |
| 2003/0202180 A1 | 10/2003 | Gobel et al. | |
| 2004/0012781 A1 * | 1/2004 | Gehrlein et al. ............. | 356/328 |
| 2005/0167621 A1 | 8/2005 | Zeng et al. | |
| 2006/0132796 A1 | 6/2006 | Haran | |

FOREIGN PATENT DOCUMENTS

| | | |
|---|---|---|
| JP | 04313007 A | 11/1992 |
| WO | WO 2005/106387 A | 11/2005 |

* cited by examiner

*Primary Examiner*—F. L Evans
(74) *Attorney, Agent, or Firm*—Scully, Scott, Murphy & Presser PC

(57) ABSTRACT

A spectroscopic sensor for measuring flat sheet product is disclosed. The disclosed sensor uses a combination of spectrometers and single-channel detectors and filters together with a broadband source of illumination to optimally measure multiple properties of a flat sheet product. A spectrometer is used to measure over a spectral range where an easily configurable set of wavelength channels is needed and where the signal-to-noise ratios and spectral resolutions of the channels are consistent with the spectral range and number of pixels of the spectrometer; while one or more single channel detector and filter combinations are used to measure, with high signal-to-noise ratio, at specific wavelengths within or outside the spectral range of the spectrometer(s). Therefore, the single channel detectors can be used to complement the information provided by a spectrometer or to extend the working range of a spectrometer by providing single wavelength measurements anywhere in the visible, near-IR or mid-IR spectral regions.

18 Claims, 3 Drawing Sheets

SPECTROSCOPIC SENSOR FOR MEASURING SHEET PROPERTIES

CROSS-REFERENCE TO RELATED APPLICATION

The present application claims priority from U.S. provisional application 60/754,767 filed on Dec. 29, 2005.

BACKGROUND OF THE INVENTION

1. Field of the Invention

The invention relates to optical sensors for the paper and plastics flat sheet industries, and more particularly, to a spectroscopic sensor for measuring characteristics of flat sheet products.

2. Discussion of the Prior Art

In the paper and plastics industries, during the process of manufacture of flat sheet products, various sheet properties of multi-layered and single layer sheets can be detected with visible and infrared radiation while the sheet making machine is operating. Multiple components of the sheet including basis weight, coating weight, moisture content, opacity and layer thicknesses can be measured by sensors which detect the amount of radiation that the sheets absorb, transmit or reflect from a beam of infrared light or other radiation. In systems employing such sensors, radiation that interacts with the sheet is typically compared at two different wavelength bands, a reference wavelength band and a measurement wavelength band, to measure different properties of flat sheet products.

FIG. 1 illustrates a typical prior art sensor configuration. An infrared (IR) radiation source 103 directs a beam of IR radiation 101 towards a sample 110. The beam is transmitted through beam conditioning optics, such as collimating lenses and/or focusing lenses 190, 192, 146, 195. These lenses condition the optical radiation for optimal sensor efficiency. The optics 146, 195 in front of the detectors 145, 135, respectively, are typically focusing lenses and those adjacent to the sample are typically collimating or focusing lenses 190, 192. IR radiation is partly absorbed, reflected and transmitted by the sample 110 depending on its various properties. Beam splitter 120 splits the IR radiation into two separate beams 118 and 128. Each beam is directed to a separate bandpass filter 170 and 160, respectively, each of which is positioned and aligned immediately before detector 135 and 145, respectively. The bandpass filters 170 and 160 are configured to pass IR radiation at selected regions of the infrared spectrum. Any IR radiation not within the selected region of the spectrum is reflected by the filters back to the beam splitter 120.

Depending on the intensity of the radiation detected at the detector, the detector generates an analog electrical signal which may be converted to a digital signal for observation. The described sensor arrangement can measure different properties of the sample under observation. For instance, in the thickness measurement of thin plastic films, one of the two infrared bandpass filters only passes infrared radiation having wavelengths in a selected region of the infrared spectrum. This first region of the spectrum is called the "reference" region, and the associated detector is called the "reference" detector. The reference channel spectral range is located in a specific region of the IR spectrum which is not associated with a signature absorption band of the material or materials which the film is composed of. This reference channel however should be indicative of all other optical loss mechanisms in the sensor system and sheet that are not indicative of the optical absorption of the material being sensed. These other properties may include such things as scattering loss from the sheet or the insertion losses of the optical components used in the sensor system.

A second bandpass filter is associated with the second infrared detector and passes only wavelengths in a second selected region of the infrared spectrum. This second region of the spectrum is called the "measure" region. The detector associated with the "measure" region of the spectrum is called the "measure" detector. The wavelength region of the measure channel is chosen to encompass an IR spectral range that is characteristic of an optical absorption band associated with the material being sensed. The optical losses in the measure channel ideally include all the same losses that are associated with the reference channel in addition to the characteristic absorption band of the material being sensed. If a comparison is made between the optical signals detected by the reference and measure channels then we can ascertain the amount in terms of weight or thickness of the material being sensed.

The arrangement described consists of two single channel detectors—one reference and one measure. A pair of detectors will typically measure a single constituent component of the sheet such as total thickness, moisture or cellulose weight. However, often multiple characteristics or multiple components of the sample need to be measured. For example, when measuring a plastic sheet that is composed of multiple components, the relative concentration of each component must be determined. By necessity, this means looking at a wider spectrum so that multiple components of the sample can be measured at the same time. This can be done by stacking reference and measure channel pairs which have had their filters chosen for each constituent component of the sheet. Occasionally common reference channels can be used hence eliminating one or more of the reference channels.

An alternative to using multiple pairs of single detectors with filters is to use an optical spectrometer. An optical spectrometer can provide a convenient method of measuring properties of light over a larger, continuous portion of the spectrum while achieving improved spectral resolution. The spectrometer outputs light intensity as a function of wavelength over a specific range of wavelengths which is split up into pixels. For example the PSG2.2 InGaAs spectrometer from Zeiss covers a spectral range of 1000 to 2150 nm with 256 pixels and has a spectral resolution of 16 nm. Another example is the PSG1.7 InGaAs spectrometer from Zeiss which covers a spectral range of 960 to 1690 nm with 512 pixels and has a spectral resolution of 5 nm. This increased spectral resolution and convenience of a spectrometer is typically obtained at the expense of signal-to-noise ratio on the intensity measurement. Also, in the design of spectrometers one can trade off spectral resolution for spectral range.

Visible, near-IR and mid-IR sensors share a common need for large spectral range, high spectral resolution and high signal-to-noise ratio. Spectral range is needed for the sensor to address a large number of applications whereas spectral resolution and signal to noise ratio are key to good sensor accuracy and repeatability. However, these requirements are usually mutually exclusive. For example, a single detector plus filter combination that allows for high signal to noise ratio and good spectral resolution does not provide broad spectral range. Conversely, a compact spectrometer provides high spectral range with good spectral resolution but at the expense of signal-to-noise ratio and hence repeatability.

Additionally, spectrometers can cover a wide spectral range but, due to practical and technical reasons, a single spectrometer does not cover the entire range between the visible and the mid-IR range. Applications where this is an issue can be found in the plastic and paper industries. For example, a single sensor is desired to measure the thickness of thin plastic films on biaxial film production lines. The very thin films can be measured using interferometry in the visible or near-infrared spectrum where absorption is weak, whereas thicker films (greater than 15-20 µm) and edge beads are measured using absorption further out in the near-infrared spectrum. Commonly assigned U.S. Pat. No. 7,088,456 to Germanenko et al. discloses a system and method for analyzing characteristics of thin films using IR sensors; this patent is incorporated herein by reference. Similarly, moisture or coat weight in paper applications and thickness in plastic applications are measured in the near-IR spectrum while opacity is measured in the visible spectrum. In the above described cases, a single spectrometer or single channel detector and filter combinations cannot fully address the measurement needs. Many types of spectrometers exist, including array spectrometers, Fourier Transform Infrared (FTIR) spectrometers, Acousto-Optic Tunable Filter (AOTF) spectrometers, Linear Variable Filter (LVF) spectrometers and Fabry-Perot spectrometers. However, at present, no single spectrometer is available with required noise characteristics, spectral resolution (i.e. number of elements), and wavelength range.

In prior art optical sensors are designed either with a spectrometer or individual filter and detector combinations.

BRIEF SUMMARY OF THE INVENTION

The present invention provides a sensor apparatus or "sensor" which combines one or more optical spectrometers with one or more single channel filter and detector combinations to improve resolution, signal-to-noise and spectral range capabilities. This allows us to realize many measurements with one sensor package which is more economical, compact and practical than using multiple sensors.

In one embodiment, the invention is a sensor for measuring characteristics of a flat sheet product, said sensor comprising: on one side of the flat sheet product, a source for emitting radiation towards the flat sheet product; and on the other side of the flat sheet product, a plurality of beam splitters arranged in series for splitting the radiation after the radiation interacts with the flat sheet product; an optical spectrometer, and a plurality of bandpass filters for filtering the radiation, each bandpass filter is coupled to a single channel detector. In another embodiment, more than one spectrometer is used.

In another embodiment, the source for emitting radiation is on the same side of the flat sheet product as the beam splitters, the bandpass filters and detectors, and the optical spectrometer. In yet another embodiment, more than one spectrometer is used.

BRIEF DESCRIPTION OF THE DRAWINGS

The invention is further described in the detailed description that follows, by reference to the noted drawings by way of non-limiting illustrative embodiments of the invention, in which like reference numerals represent similar parts throughout the drawings. As should be understood, however, the invention is not limited to the precise arrangements and instrumentalities shown. In the drawings.

DETAILED DESCRIPTION OF THE INVENTION

Reference will now be made in detail to the preferred embodiments of the present invention, a spectroscopic sensor for measuring properties of flat sheet products, examples of which are illustrated in the accompanying drawings. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of the present invention, numerous specific details are set forth in order to provide a thorough understanding of the present invention. However, it will be recognized by one of ordinary skill in the art that the present invention may be practiced without these specific details. In other instances, well known methods, procedures, components, and circuits have not been described in detail as not to unnecessarily obscure aspects of the present invention.

The inventive sensor combines the relatively large but finite spectral range of a spectrometer with relatively high signal-to-noise ratio capabilities of single channel detectors which at the same time extend the spectral range of the entire optical sensor beyond the capabilities of commercially available spectrometers. The spectrometer operates in the region where spectral range and/or resolution is needed while single channel detector and bandpass filter combinations measure, with high signal-to-noise ratio, specific wavelengths within or outside of the spectral range of the spectrometer. Therefore, the single channel detectors can be used to complement the information provided by a spectrometer or to extend the working range of a spectrometer only sensor by providing single wavelength measurements anywhere in the visible, near-IR or mid-IR.

Figure 1:
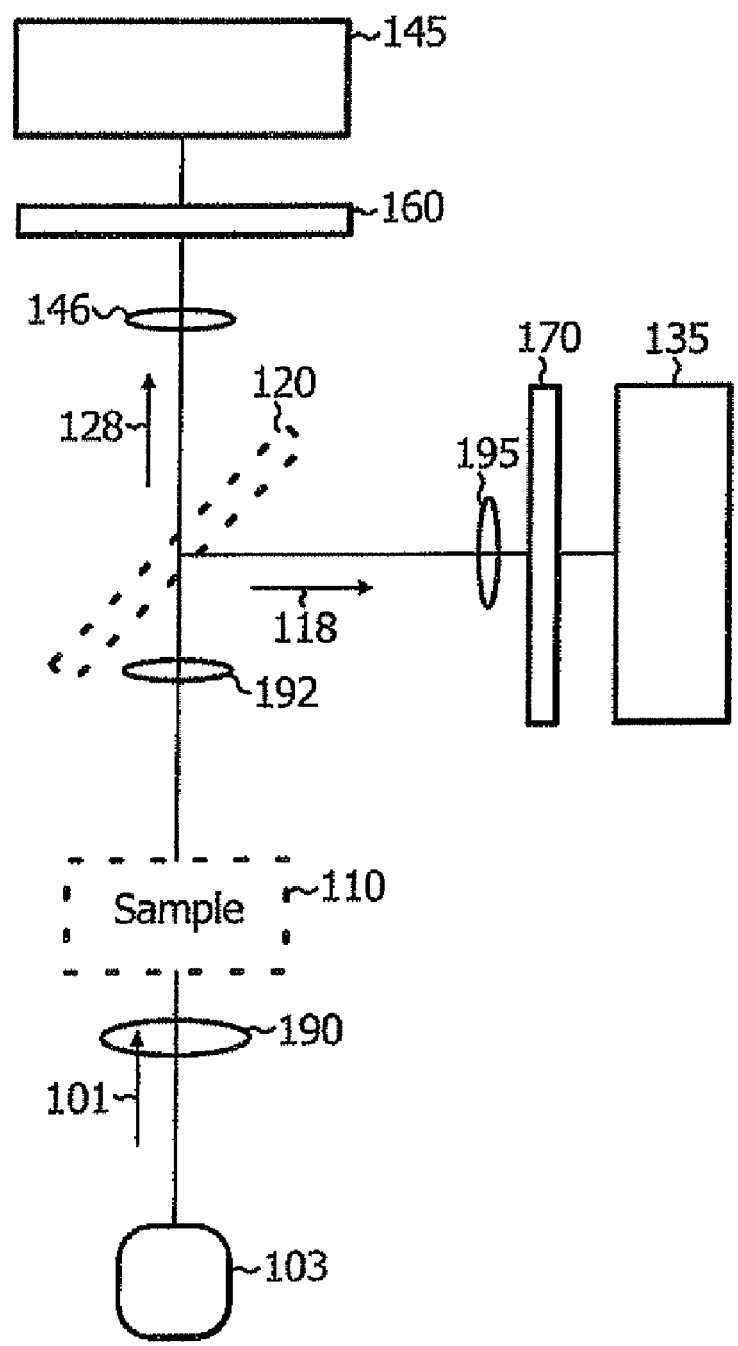
FIG. 1 is a schematic diagram of a conventional sensor configuration.
Figure 2:
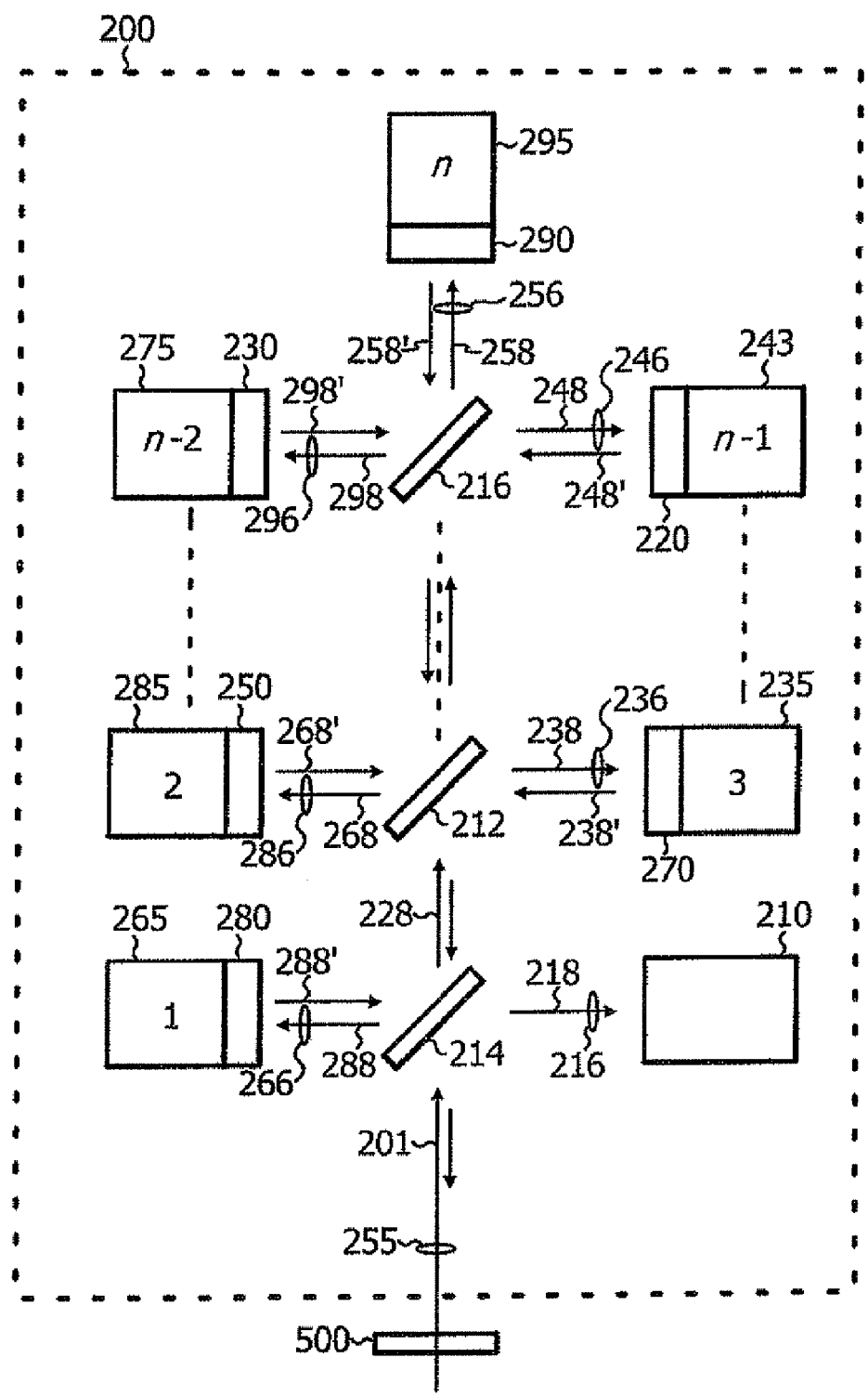
FIG. 2 is a schematic diagram of a sensor including a spectrometer in accordance with an embodiment of the invention.

Referring to FIG. 2, there is shown a schematic diagram of an exemplary embodiment of the spectroscopic sensor receiver 200 in accordance with the invention which includes a spectrometer and n single channel filter and detector combinations. Each filter and detector combination (e.g., 1, 2, 3 . . . n) may be dedicated to the detection of one part of the radiation spectrum while the spectrometer 210 provides detection over a wide range and typically with high spectral resolution of a different part of the radiation spectrum. The spectrometer could be a grating based or Linear Variable Filter (LVF) based array spectrometer, such as, for example, extended InGaAs, InGaAs, PbS, PbSe, Silicon, or MCT, etc., array spectrometers. However we are not limited to array based spectrometer and could use spectrometer such as Acousto-Optic Tunable Filter (AOTF) spectrometer, Fourier Transform InfraRed (FTIR) spectrometer and Fabry-Perot spectrometer. The extended InGaAs array would typically be sensitive to wavelengths between 1.6 and 2.55 microns and could contain 256 or 512 elements. The 256 element InGaAs array would have a resolution of approximately 12 nm. The PbS array spectrometer would typically have a 256 element array and be sensitive between 1.6 and 2.9 microns with an approximate 15 nm spectral resolution.

In an array spectrometer, the wavelength dispersive optical component can be a grating or a linear variable filters (LVF). An AOTF spectrometer uses a tunable filter and a single channel detector such as a InGaAs, PbS, PbSe, Si, MCT, etc. detector. Commonly assigned U.S. patent application Publication No. 20060132796 to F. Haran discloses a system and method for analyzing characteristics of flat sheet products using an AOTF spectrometer. This patent application is incorporated herein by reference. FTIR and Fabry-Perot spectrometers are conventional scanning interferometers. A scanning Fabry-Perot MEMS based spectrometer can be purchased from AXSUN technologies Inc., of Billerica, Mass., USA.

Radiation 201 from a sample or flat sheet product 500 is transmitted through a collimating optical lens 255 to produce light which is directed to a beam splitting means. The collimating optical lens conditions the optical radiation that has interacted with the flat sheet product 500. More specifically the collimating lens produces minimal divergence (for a given aperture) of the optical beam for transmission through the beam splitters and filters. The focusing lens 216 concentrates the filtered optical radiation onto the spectrometer 210, while the additional focusing lenses 236, 246, 256, 266, 286, 296 concentrate the filtered optical radiation onto the detector elements 235, 245, 295, 265, 285 and 275, respectively.

A beam splitting means 214, disposed at an incident angle of 45 degrees to the radiation from the sample, splits the radiation beam into two components 218 and 228. One component 218 of the radiation beam is transmitted through beam conditioning optic or focusing lens 216 and input to a spectrometer 210. The beam splitting means 214 is configured so that the spectrometer receives the proper intended wide spectrum of the radiation 201. In one embodiment, the beam splitting means is a partially transmitting mirror. This may be a plate of glass with a thin coating of metal with the thickness of the metal coating such that, of light incident at a 45 degree angle, a fraction is transmitted and the remainder is reflected. Angles other than 45 degrees can be used for the light incident, and the beam splitting means can be adjusted accordingly. Instead of a metal coating, a dielectric optical coating may also be used. In long wavelength applications where transmission through glass is weak, a semiconductor such as Silicon can be used as a substrate. In a preferred embodiment, the beam splitting means is a dichroic beam splitter which can be configured for high transmissivity for certain parts of the radiation spectrum and/or highly reflective of certain other parts of the radiation spectrum. One such beam splitter is disclosed in U.S. Pat. No. 6,961,126, entitled "Optical Wavelength Splitter," which is herein fully incorporated by reference.

FIG. 2 further illustrates that another component of the radiation 228 is provided to another beam splitting means 212. Additionally, in this embodiment, the second beam splitting means 212 outputs two components of the radiation, one 224 to the next beam splitting means and a second 238 through a lens 236, to bandpass filter 270 and detector 235. The nth beam splitting means 216 shown in FIG. 2 outputs two components of radiation 248, and 258, each of which passes through a lens 246, 256, respectively, to a bandpass filter 220, 290 and detector 245, 295, respectively. While not shown, additional beam splitting means can be added as needed; these additional beam splitting means will each produce two components of the radiation, one of which will go to the next beam splitting means while the other component will travel through a lens to a filter and detector. The exemplary embodiment shown in FIG. 2 illustrates interference filters in which the stop band is reflected and the pass band is transmitted. However, absorptive filters can also be used in which the pass band is transmitted and the stop band is absorbed.

Each bandpass filter acts to allow radiation transmission in a narrow designated spectrum, while reflecting back radiation which is not in the designated spectrum. Therefore, filters 280, 250, and 230 receive spectrum which is not in the designated bands of bandpass filters 220, 270 and 290. This is illustrated in FIG. 2 by the radiation components 288, 268 and 298, which are created by radiation components 238', 248', 258' reflecting off filters 270, 220 and 290, respectively, and passing through or reflecting off beam splitting means 214, 212 and 216. The beam conditioning optics 216, 236, 246, 256, 296, 286, 266 focus the beam into the spectrometer 210 and respective detectors 235, 245, 295, 275, 285, 265. The detectors 235, 245, 295, 275, 285 and 265 produce a current signal indicative of the intensity of the spectrum in a specific wavelength band.

It will be appreciated that an arbitrary number n of filter and detector combinations may be provided, subject only to the physical limitations of the sensor receiver 200. For purposes of illustration, the spectrometer 210 has been illustrated in one position with respect to the radiation beams, however, it will also be appreciated that the spectrometer may be placed in any position within the sensor receiver 200.

Although the previous description suggests that the reference and measure channels for a particular component are both obtained from a detector/filter combination or are both obtained from a spectrometer it is also possible to obtain the reference signal from a detector/filter combination and the measure signal from a spectrometer, or vice versa. It is also possible to use one reference channel with more than one measurement channel to obtain multiple components in the sheet.

Further, the illustrated combination of a spectrometer with detector and filter combinations is shown in a transmission geometry. That is, the sensor receiver 200 is placed on one side of the sample 500 being measured while the source of radiation is on the other side of the sample. However, it will be appreciated that the sensor 200 functions in a reflection geometry as well. That is, the source of the radiation and the sensor receiver 200 can both be placed on the same side of the sample 500.

It is standard practice to use broadband light sources which span both the visible and IR part of the radiation spectrum. This makes it possible to obtain measurements in the visible and the IR parts of the spectrum where one region is measured using a filter and detector combination and the other is measured using a spectrometer. For example, in the paper industry, the radiation source beam may combine the near-IR spectrum which is indicative of moisture content or coat weight in the paper sample with radiation in the visible spectrum which is indicative of the opacity properties of the paper sample.

In thin plastic film applications, accurate thickness measurement across the full width of the sheet is required. Thickness of the very thin grades (below 10-15 microns) can be measured using thin film interferometry techniques. However, thickness of the thicker grades and of the edge beads for all of the grades is measured using absorption techniques. One embodiment of a thin plastic film sensor is the combination of a visible or near-IR spectrometer with filter and detector combinations sensitive to the mid-IR. The thin film interferometry technique requires the spectral range and spectral resolution of the spectrometer in a spectral region where absorption is weak. The absorption technique requires measurements at specific wavelengths in regions where absorption is significant. The combination of a visible or near-IR spectrometer with filter and detector combinations in the near to mid-IR allows the two complementary techniques to be used in one sensor.

Figure 3:
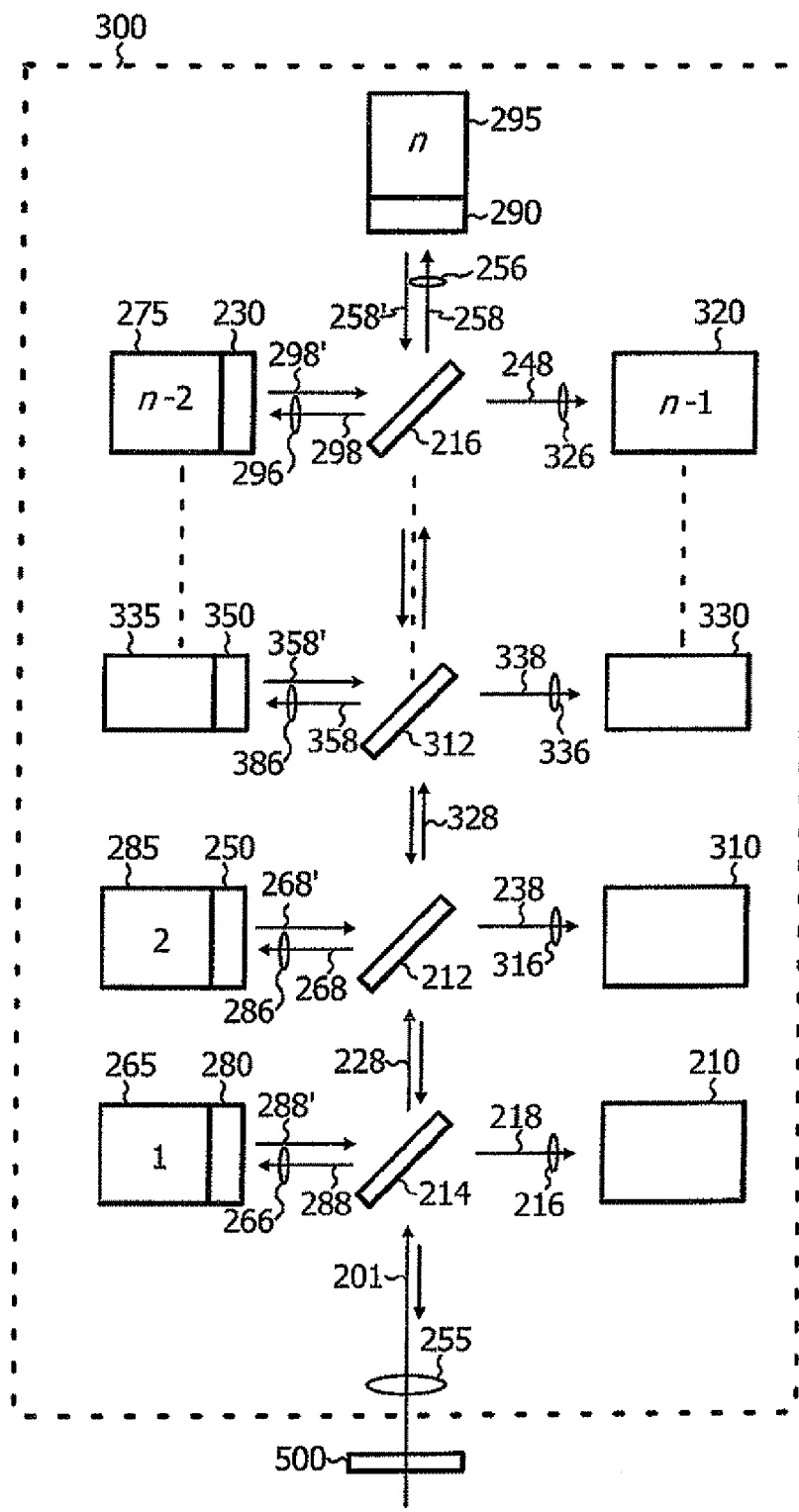
FIG. 3 is a schematic diagram of a sensor including multiple spectrometers, in accordance with another embodiment of the invention.

Referring now to FIG. 3, a second exemplary embodiment of the invention is shown. As in the embodiment shown in FIG. 2, a radiation beam 201 passes through a sample 500 and into the sensor receiver 300. Once in the receiver, the radiation beam 201 passes through beam conditioning optics 255 to the beam splitter 214. The radiation beam is split into two components 218 and 228, one of which is passed to the spectrometer 210, the second of which is passed to the next beam splitter 212. This next beam splitter also creates two radiation components 238, and 328. In this embodiment, however, radiation component 238 passes through a focusing lens 316 to a spectrometer 310 and radiation component 328 continues to the next beam splitter 312. Further, each beam splitter creates two radiation components, one of which passes to the next beam splitter. The second radiation component 338 passes through focusing lens 336 to the spectrometer 330. The nth beam splitting means 216 outputs two components of radiation 248, 258, one of which 258 is shown passing though focusing lens 256 and into the filter 290 and detector 295. The second radiation component passes through lens 326 to the spectrometer 320. Similar to the first embodiment, in the second embodiment, each bandpass filter acts to allow radiation transmission in a narrow designated spectrum, while reflecting back radiation which is not in the designated spectrum. Therefore, filters 280, 250, 350, and 230 receive spectrum which is not in the designated bands of bandpass filter 290. This is illustrated in FIG. 3 by the radiation components 288, 268, 358, and 298, which are created by radiation reflecting off filter 290 and passing through or reflecting off beam splitting means 214, 212, 312 and 216.

It will be appreciated that an arbitrary number n of filter and detector combinations and an arbitrary number m of spectrometers may be provided, subject only to the physical limitations of the sensor receiver 300. For purposes of illustration, the spectrometers have been illustrated in one position with respect to the radiation beams, however, it will also be appreciated that the spectrometers may be placed in any position within the sensor receiver 300.

The preferred embodiment of the present invention, a spectroscopic sensor for measuring flat sheet products, is thus described. While the present invention has been described in particular embodiments, it should be appreciated that the present invention should not be construed as limited by such embodiments, but rather construed according to the below claims.

What is claimed is:

1. A sensor for measuring a plurality of characteristics of a flat sheet product, said sensor comprising:
   a source for emitting radiation towards the flat sheet product;
   a plurality of beam splitters arranged in series for splitting the radiation after the radiation interacts with the flat sheet product;
   a plurality of bandpass filters for filtering the split radiation;
   a plurality of single channel detectors, each channel detector being coupled to one bandpass filter; and
   at least one optical spectrometer, wherein the at least one optical spectrometer measures one or more characteristics of said plurality of characteristics of the flat sheet product using said split radiation received from a first beam splitter of said plurality of beam splitters, and each coupled channel detector and bandpass filter measures one or more characteristics of said plurality of characteristics of the flat sheet product using said split radiation received from one or more of said plurality beam splitters, said characteristics measured by each coupled channel detector and bandpass filter being different from said characteristics measured by said spectrometer.

2. The sensor of claim 1, wherein said source is on one side of said flat sheet product and said beam splitters, said bandpass filters, and said at least one optical spectrometer are on the other side of the flat sheet product.

3. The sensor of claim 1, wherein said source is on one side of said flat sheet product and said beam splitters, said bandpass filters, and said optical spectrometer are on the same side of the flat sheet product.

4. The sensor of claim 1, further comprising beam conditioning optics for directing the radiation to the flat sheet product.

5. The sensor of claim 1, further comprising one or more additional beam conditioning optics for directing the radiation to the bandpass filters.

6. The sensor of claim 1, wherein each of said beam splitters is a half-metal mirror.

7. The sensor of claim 1, wherein each of said beam splitters is dielectric coating based.

8. The sensor of claim 1, wherein each of said beam splitters is a dichoric beam splitter.

9. The sensor of claim 1, wherein each of said beam splitters is a semiconductor beam splitter.

10. The sensor of claim 1, wherein said source emits broadband optical radiation from the UV to the Mid-IR region.

11. The sensor of claim 1, wherein a spectrum characteristic of said spectrometer and the spectrum characteristic of one of said plurality of channel detectors overlap.

12. The sensor of claim 1, wherein a spectrum characteristic of said spectrometer and the spectrum characteristic of all of said plurality of channel detectors do not overlap.

13. The sensor of claim 1, wherein the spectrometer is one of in a visible spectral range, in a near infrared spectral range, in a mid-infrared spectral range, and in a far infrared spectral range.

14. The sensor of claim 1, wherein the spectrometer is an AOTF spectrometer.

15. The sensor of claim 1, wherein the spectrometer is a FTIR spectrometer.

16. The sensor of claim 1, wherein the spectrometer is a Linear Variable Filter spectrometer.

17. The sensor of claim 1, wherein the spectrometer is an array spectrometer.

18. A method for measuring a plurality of characteristics of a flat sheet product, said method comprising:
   emitting radiation towards the flat sheet product;
   splitting the radiation after the radiation interacts with the flat sheet product, said splitting performed by a plurality of beam splitters arranged in a series;
   filtering the split radiation using one of an optical spectrometer, and a plurality of bandpass filters each coupled to a channel detector, wherein the optical spectrometer measures one or more characteristics of said plurality of characteristics of the flat sheet product using said filtered split radiation, and each coupled channel detector and bandpass filter measures one or more characteristics of said plurality of characteristics using said filtered split radiation, said characteristics measured by each coupled channel detector and bandpass filter being different from said characteristics measured by said spectrometer.

* * * * *